(12) United States Patent
Saloux et al.

(10) Patent No.: US 9,865,180 B2
(45) Date of Patent: Jan. 9, 2018

(54) HEART PHANTOM ASSEMBLY

(71) Applicants: VAL-CHUM, LIMITED PARTNERSHIP, Montréal (CA); CENTRE HOSPITALIER UNIVERSITAIRE, Caen (FR)

(72) Inventors: Eric Saloux, St Manvieu Norrey (FR); François Tournoux, Montréal (CA)

(73) Assignee: VAL-CHUM, LIMITED PARTNERSHIP, Montréal, Quebec ( * ) Notice: Subject to any disclaimer, the term of this patent is extended or adjusted under 35 U.S.C. 154(b) by 0 days.

(21) Appl. No.: 14/898,520

(22) PCT Filed: Jun. 20, 2014

(86) PCT No.: PCT/CA2014/050588
§ 371 (c)(1),
(2) Date: Dec. 15, 2015

(87) PCT Pub. No.: WO2014/201571
PCT Pub. Date: Dec. 24, 2014

(65) Prior Publication Data
US 2016/0133159 A1    May 12, 2016

Related U.S. Application Data

(60) Provisional application No. 61/838,006, filed on Jun. 21, 2013.

(30) Foreign Application Priority Data

Jun. 28, 2013   (FR) ..................... 13 56324

(51) Int. Cl.
*G09B 23/28*   (2006.01)
*G09B 23/32*   (2006.01)
(Continued)

(52) U.S. Cl.
CPC ............ *G09B 23/286* (2013.01); *A61B 5/055* (2013.01); *A61B 6/583* (2013.01); *A61B 8/587* (2013.01);
(Continued)

(58) Field of Classification Search
CPC .... G09B 23/286; G09B 23/288; G09B 23/32; G09B 23/34; A61B 5/055; A61B 6/583;
(Continued)

(56) References Cited

U.S. PATENT DOCUMENTS 5,634,797 A * 6/1997 Montgomery ....... G09B 23/286
434/268
2007/0161872 A1   7/2007 Kelly et al.
(Continued)

FOREIGN PATENT DOCUMENTS

WO    2008075303 A1   6/2008

OTHER PUBLICATIONS

International Search Report for corresponding application PCT/CA2014/050588 filed Jun. 20, 2014; dated Sep. 16, 2014.

*Primary Examiner* — Lisa Caputo
*Assistant Examiner* — Nathaniel T Woodward
(74) *Attorney, Agent, or Firm* — Cantor Colburn LLP

(57) ABSTRACT

A heart phantom assembly comprises a mechanical actuator system comprising a support operatively supporting at least two actuators and a fixing device. A phantom interface is operatively connected to the at least two actuators to be displaceable in at least one translational degree of freedom and at least one rotational degree of freedom as a function of actuation from the at least two actuators. A deformable heart phantom is connected at an end to the phantom interface, and at another end to the fixing device, to be subjected to compression/expansion in response to movements of the phantom interface in the translational degree of (Continued)

freedom, and to torsion in response to movements of the phantom interface in the rotational degree of freedom.

20 Claims, 7 Drawing Sheets

(51) Int. Cl.
*A61B 6/00* (2006.01)
*A61B 8/00* (2006.01)
*G09B 23/34* (2006.01)
*A61B 5/055* (2006.01)
*G01D 18/00* (2006.01)

(52) U.S. Cl.
CPC ........... *G01D 18/00* (2013.01); *G09B 23/288* (2013.01); *G09B 23/32* (2013.01); *G09B 23/34* (2013.01); *A61B 2560/0223* (2013.01); *A61B 2576/023* (2013.01)

(58) Field of Classification Search
CPC ............ A61B 8/587; A61B 2560/0223; A61B 2576/023; G01D 18/00
USPC ........................................................ 73/866.4
See application file for complete search history.

(56) References Cited

U.S. PATENT DOCUMENTS

| 2008/0138780 | A1* | 6/2008 | Eggert | G06F 19/3437 434/266 |
| 2010/0047752 | A1* | 2/2010 | Chan | B29C 33/3857 434/272 |
| 2010/0167251 | A1* | 7/2010 | Boutchko | A61B 5/416 434/267 |
| 2012/0123592 | A1 | 5/2012 | Carignan et al. | |
| 2014/0069215 | A1* | 3/2014 | Tavakoli | A61B 6/583 73/866.4 |
| 2016/0027345 | A1* | 1/2016 | Carson | G09B 23/288 434/262 |

* cited by examiner

HEART PHANTOM ASSEMBLY

CROSS-REFERENCE TO RELATED APPLICATIONS

The present application claims priority on U.S. Provisional Patent Application No. 61/838,006, filed Jun. 21, 2013, and on French Patent Application No. 1356324, filed on Jun. 28, 2013.

TECHNICAL FIELD

The present application relates to a dynamic heart phantom assembly for the validation, standardization and calibration of imagery systems for non-invasive cardiovascular imagery.

BACKGROUND OF THE ART

Non-invasive cardiovascular imagery has become increasingly important in the diagnostic, therapeutic evaluation and pronostic determination of cardiovascular diseases. The development of such imagery has allowed the measurement and evaluation of the cardiac function. Prior to the development of cardiovascular imagery, the cardiac function was essentially limited to visual appreciation of the overall cardiac function based on endocardial excursion and parietal thickening. Such methods are based on the experience of the assessor and have a considerable suggestive component.

Recent developments in non-invasive cardiovascular imagery aim to quantify the myocardial function based on the measure of deformation and displacement of muscles tissue. These measurements, in two or three dimensions, may be obtained using ultrasounds, X-rays, magnetic resonance or nuclear medicine. However, the complexity and diversity of algorithms used may slow down the processing of the data and hence delay the acquisition of the results. Hence, the improvement of imagery systems may gain in accuracy and precision by the development of reliable cardiac phantom model, for instance to test the calibrate imagery systems.

SUMMARY

It is therefore an aim of the present disclosure to provide a heart phantom assembly that addresses issues associated with the prior art.

Therefore, in accordance with the present disclosure, there is provided a heart phantom assembly comprising: a mechanical actuator system comprising a support operatively supporting at least two actuators and a fixing device, and a phantom interface operatively connected to the at least two actuators to be displaceable in at least one translational degree of freedom and at least one rotational degree of freedom as a function of actuation from the at least two actuators; and a deformable heart phantom connected at an end to the phantom interface, and at another end to the fixing device, to be subjected to compression/expansion in response to movements of the phantom interface in the translational degree of freedom, and to torsion in response to movements of the phantom interface in the rotational degree of freedom.

Further in accordance with the present disclosure, liquid injection means are connected to the phantom interface and in fluid communication with the deformable heart phantom to inject liquid therein to inflate the deformable heart phantom.

Still further in accordance with the present disclosure, a conduit in the phantom interface is in fluid communication with an inner cavity of the deformable heart phantom and with the liquid injection means, for injection of fluid therethrough.

Still further in accordance with the present disclosure, the mechanical actuator system comprises three of the actuators, with one of the actuators configured to provide the one translational degree of freedom, another of the actuators configured to provide the one rotational degree of freedom, and another of the actuators configured to actuate the liquid injection means.

Still further in accordance with the present disclosure, one of the actuators configured to provide the one translational degree of freedom is a linear actuator, with a direction thereof parallel to a longitudinal axis of the heart phantom.

Still further in accordance with the present disclosure, the one of the actuators configured to provide the one rotational degree of freedom is a linear actuator, with a direction thereof transverse to a longitudinal axis of the heart phantom, with a rack and pinion assembly operatively connecting the actuator to the phantom interface.

Still further in accordance with the present disclosure, the heart phantom has a flange at an end thereof configured for connection with the fixing device.

Still further in accordance with the present disclosure, the flange is a monolithic part of the heart phantom.

Still further in accordance with the present disclosure, the heart phantom has a ring-shaped part at an end thereof configured for connection with the fixing device.

Still further in accordance with the present disclosure, the ring-shaped part is made of a material having a greater hardness than that of a deformable body of the heart phantom.

Still further in accordance with the present disclosure, the ring-shaped part is comolded with the heart phantom.

Still further in accordance with the present disclosure, the ring-shaped part has a central toothed opening.

Still further in accordance with the present disclosure, the heart phantom has an outer cylindrical surface.

Still further in accordance with the present disclosure, the heart phantom has an ogive-shaped inner cavity.

Still further in accordance with the present disclosure, a surface of an inner cavity of the heart phantom has a plurality of hollows and protrusions.

Still further in accordance with the present disclosure, an apical component is at an end of the heart phantom, the apical component having a curved convex portion received in a cavity at an end of the heart phantom.

Still further in accordance with the present disclosure, the at least two actuators are pneumatically actuated.

Still further in accordance with the present disclosure, a casing defines an inner cavity, the inner cavity configured for receiving the deformable heart portion and at least a part of the mechanical actuator system.

Still further in accordance with the present disclosure, the casing has a narrower end configured to receive the heart phantom, and a larger end configured to receive at least part of the mechanical actuator.

Still further in accordance with the present disclosure, actuators are in the casing between the support of the mechanical actuator system and the casing configured for displacing the heart phantom assembly in the inner cavity of the casing.

Still further in accordance with the present disclosure, windows are on at least one side and on an end of the casing adjacent to the heart phantom.

DETAILED DESCRIPTION

Figure 1:
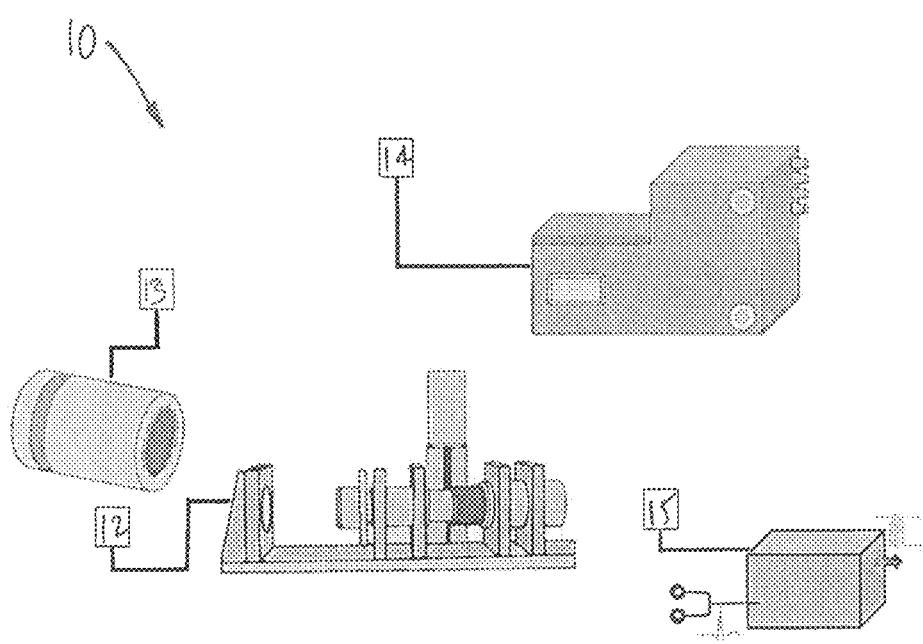
FIG. 1 is a schematic exploded view of components of a heart phantom assembly of the present disclosure.

Referring to the drawings and more particularly to FIG. 1, a heart phantom assembly in accordance with the present disclosure is generally shown at 10. The heart phantom assembly 10 may have a mechanical actuator system 12, a heart phantom 13, a casing 14, and a controller 15. As a whole, the heart phantom assembly 10 is designed to be used with different imagery systems, including ultrasound, magnetic resonance imagery (MRI) and X-rays among other possibilities, with the heat phantom assembly simulating myocardial function for imaging purposes.

The mechanical actuator system 12 supports the phantom 13 and performs movements on the phantom 13 to replicate myocardial function. According to an embodiment, the mechanical actuator system 12 provides by itself the necessary degrees of actuation to simulate heart motion on the phantom 13.

The phantom 13 is a deformable gel vessel that simulates the myocardium in three-dimensional deformation capacity.

The casing 14 encloses the mechanical actuator system 12 and the phantom 13, with the possibility of submerging them in a liquid. Moreover, the casing 14 may be the interface between pneumatic, electric, and/or hydraulic networks to control the mechanical actuator system 12 and circulate liquid in the phantom 13.

The controller 15 controls the operation of the heart phantom assembly 10 and more specifically controls the operation of the mechanical actuator system 12 to deform and displace the phantom 13. The controller 15 is thus the interface by which a user may operate the heart phantom assembly 10 for imaging thereof. According to an embodiment, the controller 15 operates pneumatic valves to control the feed of compressed air to the mechanical actuator system 12. The controller 15 is typically a processing unit such as a computer, laptop, tablet, or the like running an application controlling the operation of the heart phantom assembly 10. The controller 15 may have any appropriate telecommunication arrangement (e.g., wireless), to control the heart phantom assembly 10 remotely from the imagery systems.

Figure 2:
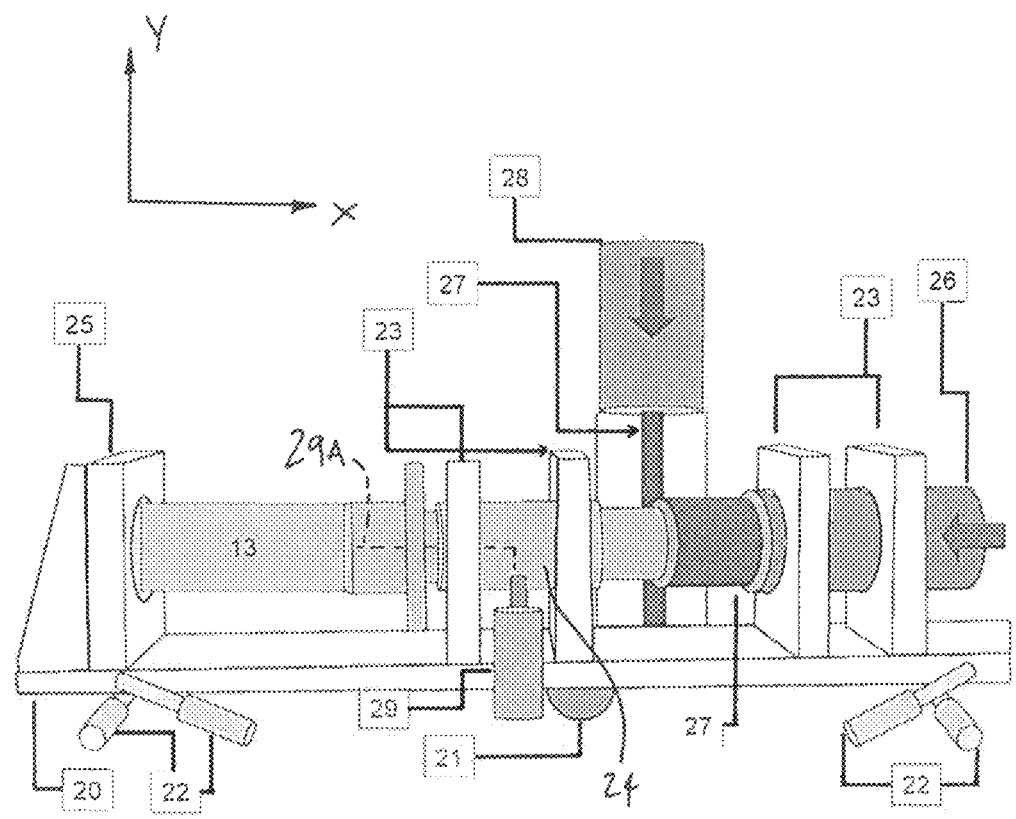
FIG. 2 is a detailed view of a mechanical actuator system with heart phantom of the heart phantom assembly of FIG. 1.
Figure 3:
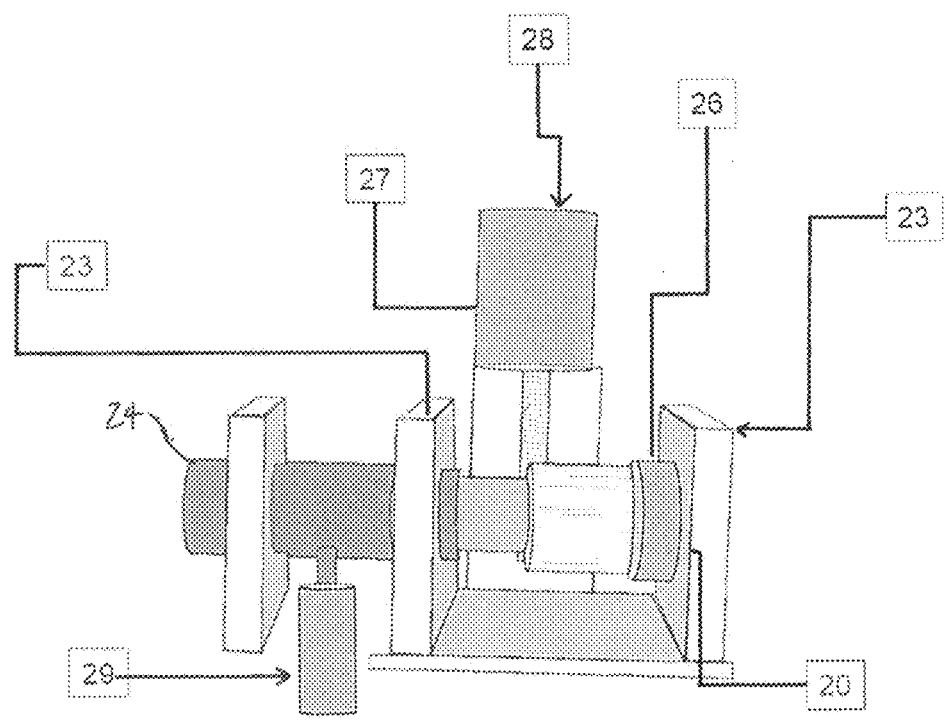
FIG. 3 is a schematic view of rack and pinions of the mechanical actuator of FIG. 2, used to transmit motion to the heart phantom.

Referring concurrently to FIGS. 2 and 3, the mechanical actuator system 12 is shown in greater detail, with FIG. 2 showing the interaction between the phantom 13 and the mechanical actuator system 12. The mechanical actuator system 12 has a structure 20 supporting its various components. The structure 20 may have any appropriate configuration but is schematically shown as having a base plate. Appropriate joints, such as rotational joint 21 and linear actuators 22, are connected to the structure 20 so as to allow integral movements of the structure 20 and the components thereon. By way of the rotational joint 21 and the linear actuators 22, the structure 20 may be moved in rotation, inclination and elevation, with respect to the casing 14 in which it will be received.

Figure 4:
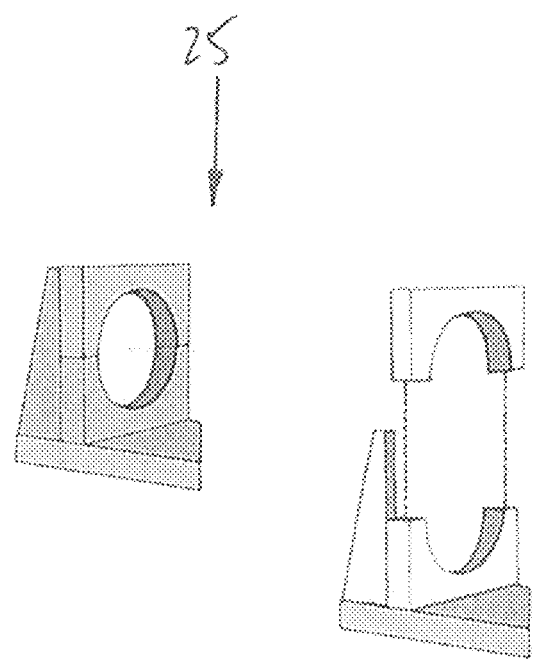
FIG. 4 is a schematic view of a phantom fixing device of the mechanical actuator of FIG. 2.

Housing plates 23 project from the base plate of the structure 20, and support movable components of the mechanical actuator system 12 in such a way that desired movements may be performed on the phantom 13. Structure 20 comprises a phantom interface 24 by which actuation components of the actuator system 12 are connected to an end of the phantom 13, to expose the phantom 13 to movements. The structure 20 further comprises a phantom fixing device 25 secured to an opposite end of the phantom 13. The phantom fixing device 25 is shown in greater detail in FIG. 4 as having a guillotine like structure to clamp onto the other end of the phantom 13, in releasable engagement. In an embodiment, the basal part of the phantom 13 is at the phantom interface 24, while the apical end of the phantom 13 is in the fixing device 25, as shown in greater detail hereinafter.

The phantom interface 24 is at an end of a linear actuator 26 supported by the housing plates 23. Hence, a translational movement of the linear actuator 26 results in a corresponding motion of the phantom interface 24, thereby compressing or stretching the phantom 13, along a longitudinal direction of the linear actuator 26, generally shown as X. A rack-and-pinion mechanism 27 as shown in FIGS. 2 and 3 is driven by a linear actuator 28 aligned along direction Y. The linear actuator 28 is in a generally transverse arrangement relative to the linear actuator 26. An output of the linear actuator 28 will result in a rotation of the phantom interface 24 about the longitudinal direction X of the linear actuator 26. This is one of numerous arrangements considered to impart a rotational motion to the phantom interface 24. This rotation of the platform interface 24 is allowed by way of the openings defined in the housing plates 23. Hence, rotation of the phantom interface 24 will result in torsion of the phantom 13 and thus compression of its material, as the phantom 13 has its ends clamped respectively by the phantom interface 24 and the fixing device 25. The phantom interface 24 may therefore be displaceable in at least a rotational degree of freedom and a translational degree of freedom relative to the structure 20. A third actuator 29 may be connected to the phantom interface 24 in order to inject liquid within the phantom 13. This injection may result in the expansion of the phantom 13 with a thinning of its walls, along a radial direction. The phantom interface 24 therefore comprises suitable conduits to be in fluid communication with the phantom 13 to fill same. Likewise, the phantom 13 may have an opening in line with the conduits 29A of the phantom interface 24 to receive the fluid. To avoid the presence of air bubbles within the phantom 13, a membrane (of latex for example) can be positioned within the phantom interface 24 to allow the pressure to be transmitted from 29 to 24 without bubbles. The actuators 26 and 28 may be operated simultaneously, for instance in alternating fashion with the actuator 29. It is observed that the heart phantom 13 may be deformed in radial, longitudinal, circumferential and rotation directions, by its interaction with the phantom interface 24. As the distance between the phantom interface 24 and the fixing device 25 is adjustable by displacement of the phantom interface 24, heart phantoms of different dimensions can be used with the mechanical actuator system 12.

Figure 5:
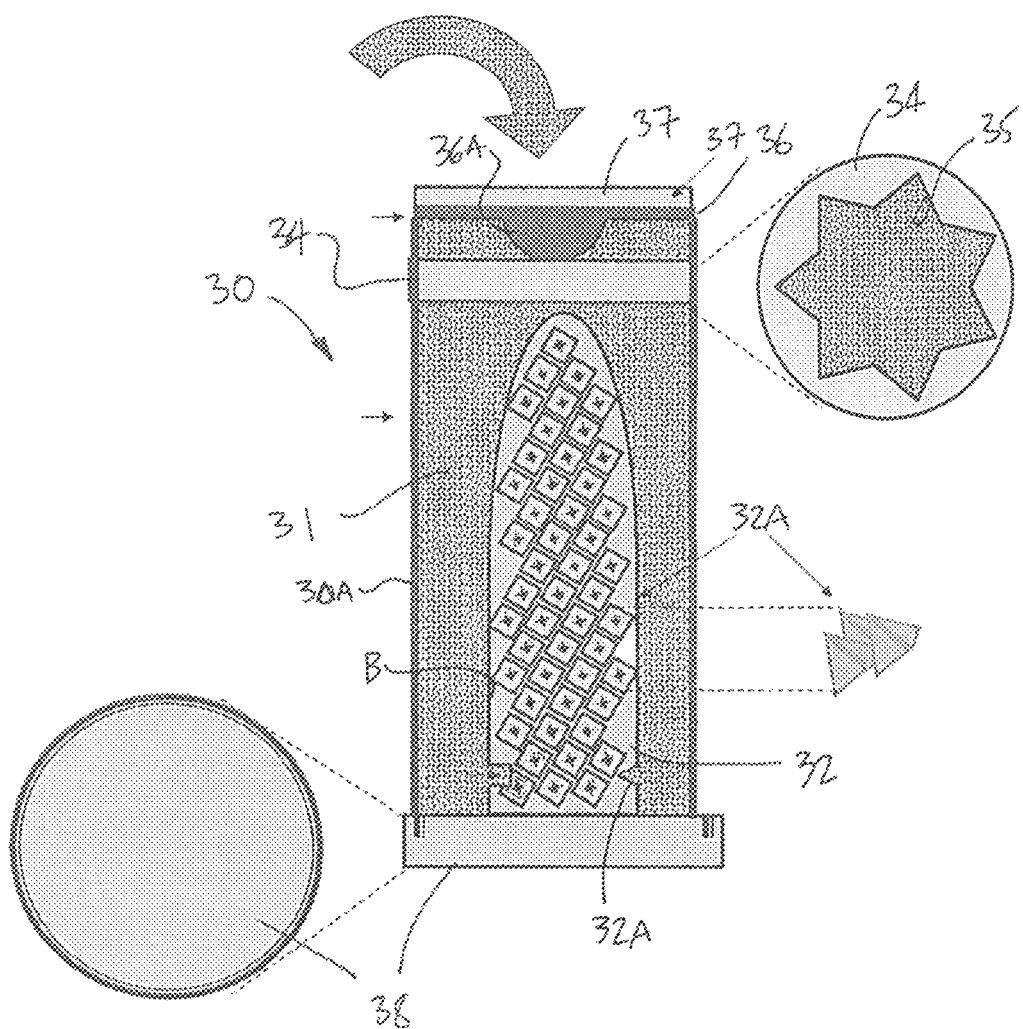
FIG. 5 is a schematic view of a mold for a phantom of the heart phantom assembly of FIG. 1.

The phantom 13 is or has a hollow cavity made of resilient material simulating that myocardial muscle. For instance, the phantom 13 may be molded or fabricated with a polyvinyl alcohol gel. The gel is a systolic type gel, with the cavity of the phantom 13 being an expandable volume. According to an embodiment, the phantom 13 is molded from the appropriate gel mixed with a speckle additive such as graphite powder. Markers, for instance in the form of crystals embedded in the gel, may be used for sonomicrometry applications. In an embodiment, the polyvinyl undergoes freezing/thawing cycles to reach elastic and acoustic properties replicating that of the myocardial muscle. By way of example, there is illustrated in FIG. 5 a mold 30 that could be used to manufacture the phantom 13. The mold 30 is shown as having a cylindrical wall 30A extending along longitudinal axis X. The wall 30A defines a cavity 31 of cylindrical shape, in which is inserted the gel to form the phantom 13. A central, for example ogive-shaped, portion 32 is in the mold, and will define the inner cavity B of the phantom 13. During the molding, the portion 32 is received in the cavity 31, to eventually define the cavity B of the body of the phantom 13. In an embodiment, gravity is used to fill the cavity 31. Hence, the phantom 13 will have a generally cylindrical outer body with an ogive-shaped cavity, representative of the shape of the cavity 31 of FIG. 5. The size of the ogive-shaped portion 32 may be varied, to produce different wall thicknesses for the heart phantom 13, and thus simulate different cardiopathy conditions. Localization markers 33 may be in the ogive-shaped portion 32, and may be useful for quantification tools.

Still referring to FIG. 5, the phantom 13 may be anchored to a ring-shaped first fixing part 34. The first fixing part 34 is to be fixed to the fixing device 25. In an embodiment, the first fixing part 34 comprises or is a cylindrical outer part, having an outer surface for application against or in the fixing device 25 to block movements therebetween. In an embodiment, the first fixing part 34 is in a material different from gel material of the phantom 13, and may hence be comolded with the gel to be an integral part of the phantom 13. In an embodiment, the first fixing part 34 is in a synthetic material, for example hard, or having a hardness higher than the gel of the body of the phantom 13. In an embodiment, the body of the phantom 13 goes through the first fixing part 34 (as in FIG. 5) and has an apical end extending beyond the first fixing part 34. In an embodiment corresponding to FIG. 5, the first fixing part 34 is transversal to a longitudinal axis of the body of the phantom 13.

In an embodiment, also corresponding to FIG. 5, the first fixing part 34 is shown as having a central toothed opening 35 and is integrally molded into or around the gel of the phantom 13. The first fixing part 34 may be used as an anchoring component for the phantom 13. Accordingly, the first fixing part 34 must not impede ultrasounds and must be profiled to avoid reflections. It is observed that the cavity 31 of the mold 30 and the body of the phantom 13 extend beyond the fixing part 34, whereby the gel end of the phantom 13 may be anchored directly to the phantom interface 24, as one possible solution, although other solutions are considered as well.

An insert 36 may also be positioned in the mold 30 to define the apical component 36A. For instance, the apical component 36A formed by the insert 36 is the gel without the graphite, and has a curved convex portion received in a corresponding cavity 36B in the phantom 13. Lid 37 and base 38 ensure the watertightness of the mold 30. Base 38 may comprise a groove to be matingly connected to the mold 30.

The mold 30 may comprise additional components, such as zones used for inserts, which inserts may be gel portions of different elasticity to mimic fibroblast zones, sonometry crystals, rubies, etc.

In an embodiment, the portion 32 of the mold has protruding parts 32A on its surface, for example tips. The protruding parts 32A serve to form hollows and protrusions in the inner wall surface of the phantom 13. Accordingly, reflections of the signal on the inner wall surface defining the inner cavity B of the phantom 13 are diminished or prevented.

Figure 6:
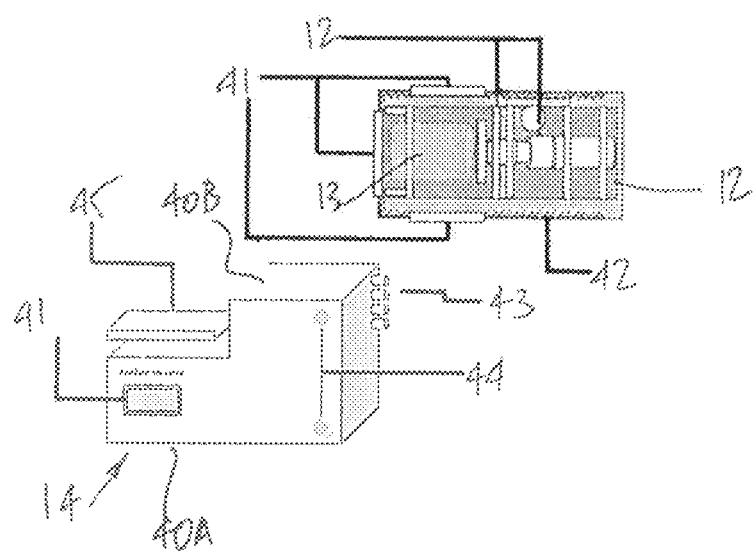
FIG. 6 shows schematic views of the mechanical actuator and phantom in a casing during use of the heart phantom assembly of FIG. 1.

Referring to FIG. 6, the casing 14 is shown in greater detail. The casing 14 has a phantom end 40A and an actuator end 40B. The casing 14 is typically made of a non-metallic material, such as high-density polyethylene or poly(methyl methacrylate), although other materials are also considered. The casing 14 has an inner cavity in which at least part of the mechanical actuator system 12 and the phantom 13 are accommodated, with the phantom 13 generally located in the narrower phantom end 40A. As observed, the phantom end 40A of the casing 14 may be of smaller dimensions, allowing same to be inserted within a MRI apparatus.

The casing 14 may have in the phantom end 40A ultrasound windows 41 on opposite sides and in alignment with the phantom 13 located in the inner cavity 40, through which windows 41 ultrasound may be performed. In order to dampen reverberations on the walls of the casing 14, an insulation membrane 42 may be applied against the surfaces of the inner cavity 40. For instance, the insulation membrane 42 is made of polyurethane foam, or like damping material.

In an embodiment, compressed air is used to actuate the linear actuators. Hence, compressed air ports 43 may be provided on the casing 14 and are connected to various linear actuators of the mechanical actuator system 12 inside the casing 14, although not shown. The compressed air ports 43 may be inlets or outlets as appropriate, and are connected to a compressed air source or network. It is pointed out that any appropriate valves may be provided in the heart phantom assembly 10, to actuate the linear actuators in deforming/displacing the heart phantom 13 to simulate cardiac function. The valves may be within the casing or located remotely therefrom. Liquid ports 44 are also provided on the casing 14 and are connected to the inner cavity 40 to submerge the phantom 13. The liquid ports 44 may be inlets or outlets as appropriate, and are connected to a liquid network (e.g., liquid source, reservoir, valves). In an embodiment, the cavity 40 is filled with deionized water. In the case of hydraulic and pneumatic connections in the assembly 10, appropriate precautions should be taken to avoid any significant fluid leaks. A cover 45 is realisably secured to the body of the casing 14 and allows access to the phantom 13 and/or components of the mechanical actuator system 12.

The material selected for the components of the heart phantom assembly 10 take into consideration the contemplated applications. For instance, the components of the heart phantom assembly 10 used in proximity to a MRI scanner in magnetic resonance applications should be non-magnetic, whereby the use of pneumatic actuation (i.e., linear actuators 22, 26, 28 and 29) is particularly well suited. Windows 41 are available for ultrasounds. Insonification of the heart phantom 13 may be performed by an insonification part from the side or the ends of the phantom 13, for example from the apical end of the phantom 13, and for example from apical component 36A (FIG. 5). In an embodiment, the apical component 36A has a curved convex portion as shown in FIG. 5, so as to diminish or prevent reflections of the signal sent by the insonification part or by any part sending any signal. Moreover, the heart phantom assembly 10 may be made of materials compatible with radiography.

The controller 15 may also be compatible with the imaging systems, for the central commanding of both the imaging system and the heart phantom assembly 10. For instance, the image acquisition may be triggered by the controller 15. For this purpose, the controller 15 may be adapted to interact with a processor of the imaging system, by any appropriate means.

Figure 7:
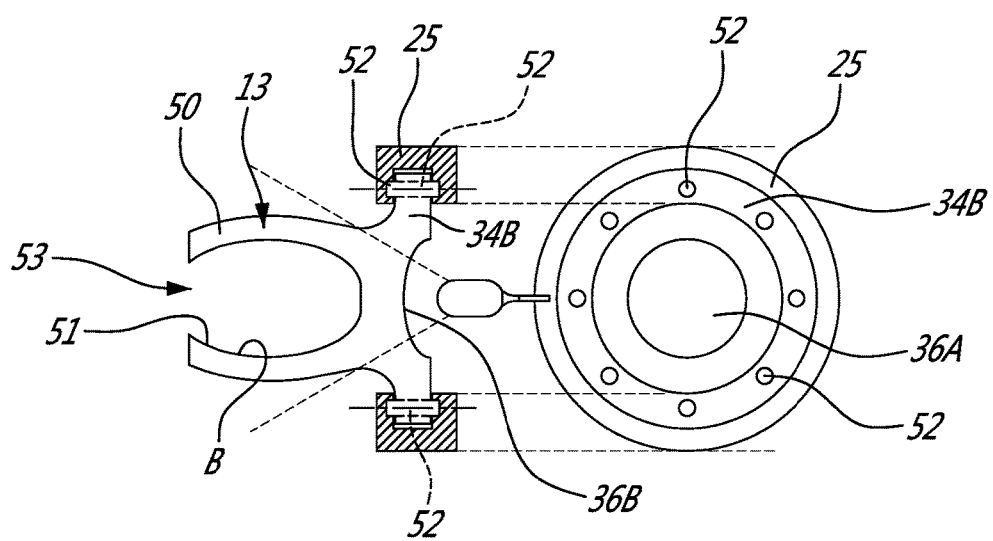
FIG. 7 is a schematic view of an embodiment of the heat phantom of FIG. 1, relative to the fixing device.

In another embodiment shown in FIG. 7, the body 50 of the phantom 13 comprises a different configuration for the first fixing part 34B, which fixing part 34B is to be fixed to the fixing device 25. In an embodiment, the first fixing part 34B has an outer surface for application against the fixing device 25. In an embodiment, the first fixing part 34B is in the same material (for example gel) as the body 50, and is thus integrally molded with the remainder of the body 50 (an hence monolithically related to the body 50 of the phantom 13). In FIG. 7, the apical component 36A is shown in greater detail, as defining a concavity, the benefits of which are described above in terms of insonofication. In FIG. 7, the first fixing part 34B is a collar, flange or a disk, extending around the apical component 36A. Still in FIG. 7, the first fixing part 34B is at a longitudinal side of the body 50 delimiting the inside cavity 51 of the phantom 13 extending along the longitudinal axis of the phantom 13. In an embodiment, the first fixing part 34B has through-holes 52 for fixing to the fixing device 25, for example by other fixing means going through the holes 52, which can be for example bolts. The body 50 has an opening 53 situated away from apical component 36A and from first fixing part 34B.

The invention claimed is:

1. A heart phantom assembly comprising:
a mechanical actuator system comprising a support operatively supporting at least two actuators and a fixing device, and a phantom interface operatively connected to the at least two actuators to be displaceable in at least one translational degree of freedom and at least one rotational degree of freedom as a function of actuation from the at least two actuators; and
a deformable heart phantom connected at an end to the phantom interface, and at another end to the fixing device, the deformable heart phantom made in a systolic condition to be subjected to compression/expansion in response to movements of the phantom interface in the translational degree of freedom, and to torsion in response to movements of the phantom interface in the rotational degree of freedom.

2. The heart phantom assembly according to claim 1, further comprising liquid injection means connected to the phantom interface and in fluid communication with the deformable heart phantom to inject liquid therein to inflate the deformable heart phantom.

3. The heart phantom assembly according to claim 2, further comprising a conduit in the phantom interface in fluid communication with an inner cavity of the deformable heart phantom and with the liquid injection means, for injection of fluid therethrough.

4. The heart phantom assembly according to claim 2, wherein the mechanical actuator system comprises three of the actuators, with one of the actuators configured to provide the one translational degree of freedom, another of the actuators configured to provide the one rotational degree of freedom, and another of the actuators configured to actuate the liquid injection means.

5. The heart phantom assembly according to claim 1, wherein the one of the actuators configured to provide the one translational degree of freedom is a linear actuator, with a direction thereof parallel to a longitudinal axis of the heart phantom.

6. The heart phantom assembly according to claim 1, wherein the one of the actuators configured to provide the one rotational degree of freedom is a linear actuator, with a direction thereof transverse to a longitudinal axis of the heart phantom, with a rack and pinion assembly operatively connecting the actuator to the phantom interface.

7. The heart phantom assembly according to claim 1, wherein the heart phantom has a flange at an end thereof configured for connection with the fixing device.

8. The heart phantom assembly according to claim 7, wherein the flange is a monolithic part of the heart phantom.

9. The heart phantom assembly according to claim 1, wherein the heart phantom has a ring-shaped part at an end thereof configured for connection with the fixing device.

10. The heart phantom assembly according to claim 9, wherein the ring-shaped part is made of a material having a greater hardness than that of a deformable body of the heart phantom.

11. The heart phantom assembly according to claim 9, wherein the ring-shaped part is comolded with the heart phantom.

12. The heart phantom assembly according to claim 9, wherein the ring-shaped part has a central toothed opening.

13. The heart phantom assembly according to claim 1, wherein the heart phantom has an outer cylindrical surface.

14. The heart phantom assembly according to claim 1, wherein the heart phantom has an ogive-shaped inner cavity.

15. The heart phantom assembly according to claim 1, wherein a surface of an inner cavity of the heart phantom has a plurality of hollows and protrusions.

16. The heart phantom assembly according to claim 1, further comprising an apical component at an end of the heart phantom, the apical component having a curved convex portion received in a cavity at an end of the heart phantom, the apical component being connected to the fixing device.

17. The heart phantom assembly according to claim 1, wherein the at least two actuators are pneumatically actuated.

18. A heart phantom assembly and casing comprising:
the heart phantom assembly according to claim 1; and
a casing defining an inner cavity, the inner cavity configured for receiving the deformable heart portion and at least a part of the mechanical actuator system, the casing being made of a non-metallic material.

19. The heart phantom assembly and casing according to claim 18, wherein the casing has a narrower end configured to receive the heart phantom, and a larger end configured to receive at least part of the mechanical actuator.

20. The heart phantom assembly and casing according to claim 18, further comprising actuators in the casing between the support of the mechanical actuator system and the casing configured for displacing the heart phantom assembly in the inner cavity of the casing.

* * * * *